United States Patent [19]

Jentsch et al.

[11] Patent Number: 5,498,744
[45] Date of Patent: Mar. 12, 1996

[54] PROCESS FOR THE PREPARATION OF DIMETHYL CARBONATE

[75] Inventors: Joerg-Dietrich Jentsch, Mülheim; Alexander Klausener, Köln; Heinz Landscheidt, Duisburg; Bernd Lenders, Krefeld; Bernd Pennemann, Köln; Erich Wolters, Köln; Eberhard Zirngbiebl, Köln, all of Germany

[73] Assignee: Bayer Aktiengesellschaft, Leverkusen, Germany

[21] Appl. No.: 273,547

[22] Filed: Jul. 11, 1994

[30] Foreign Application Priority Data

Jul. 15, 1993 [DE] Germany .................. 43 23 679.0
Jul. 15, 1993 [DE] Germany .................. 43 23 678.2
Jul. 15, 1993 [DE] Germany .................. 43 23 680.4

[51] Int. Cl.$^6$ .................................................. C07C 69/96
[52] U.S. Cl. ........................................ 558/277; 558/260
[58] Field of Search ................................ 558/277, 260

[56] References Cited

U.S. PATENT DOCUMENTS

| 5,214,184 | 5/1993 | Matuzaki et al. ............... 558/277 |
| 5,231,213 | 7/1993 | Landscheidt et al. ........... 558/277 |

FOREIGN PATENT DOCUMENTS 0503618 9/1992 European Pat. Off. .
0503091 9/1992 European Pat. Off. .
0523508 1/1993 European Pat. Off. .

OTHER PUBLICATIONS

Chinese paper with English Abstract entitled "Research Of A New Method Of Synthesis Of Dimethyl Carbonate:, Jiang Xuan–zhen, Zhu Yong–bao (Department of Chemistry, Zhejang University, Hangzhou) and Xu Song–yan (Fujian Institute of Research on the Structure of Matter, Academia Sinica," Fuzhou (1989)).

Primary Examiner—José G. Dees
Assistant Examiner—Dwayne C. Jones
Attorney, Agent, or Firm—William C. Gerstenzang; Sprung Horn Kramer & Woods

[57] ABSTRACT

Dimethyl carbonate is obtained with a high selectivity and great constancy over time by reacting carbon monoxide with methyl nitrite in a continuous gas phase reaction in the presence of a heterogeneous catalyst prepared by the application to a suitable support of one or more palladium compounds of the formula $$[Pd(N(R^1, R^2, R^3))_n]X^1_2 \qquad (I),$$

wherein $R^1$, $R^2$, $R^3$, $X^1$ and n are as defined in the disclosure, optionally in combination with one or more promoters from the group consisting of the elements Fe, Co, Ni, V, Nb, Mo, Ta, Ti, Cu and Cr, the rare earths and/or compounds thereof, and/or with one or more promoters from the group consisting of alkali metal and alkaline earth metal halides.

21 Claims, No Drawings

PROCESS FOR THE PREPARATION OF DIMETHYL CARBONATE

BACKGROUND OF THE INVENTION

1. Field of the Invention

The present invention relates to a process for the preparation of dimethyl carbonate by reacting carbon monoxide with methyl nitrite in the presence of a catalyst which has been prepared by the application to a suitable support of one or more palladium compounds with Pd-oriented N-containing ligands, optionally in combination with one or more promoters from the group comprising the elements Fe, Co, Ni, V, Nb, Mo, Ta, Ti, Cu and Cr, the rare earths and/or compounds thereof, and/or with one or more promoters from the group comprising alkali metal and alkaline earth metal halides.

2. Description of the Related Art

Dialkyl carbonates are of general chemical and industrial importance. Thus, for example, diethyl carbonate is an excellent solvent in the medium boiling range. Dialkyl carbonates are also excellent carbonylating and acylating reagents. They are of great importance in the preparation of other carbonates, for example diphenyl carbonate, urethanes and ureas. Finally, on account of their high oxygen content, they are suitable as fuel additives for improving the knock rating of motor fuels.

DESCRIPTION OF THE RELATED ART

It is known that dialkyl carbonates can be prepared by reacting phosgene or alkyl chloroformates with alcohols. There is an increasing interest, however, in superseding the use of the toxic phosgene or the intermediates derived therefrom, such as chloroformic acid esters, by other processes.

Particularly important processes here are those in which carbon monoxide is reacted in the gas phase with alkyl nitrites on heterogeneous catalysts containing platinum metals. Thus, Zeitschrift fur Katalytische Forschung (China) Vol. 10(1) pp. 75 to 78 (March 1989) describes the reaction of carbon monoxide with methyl nitrite on a supported $PdCl_2$-containing activated charcoal catalyst to form predominantly dimethyl carbonate in addition to dimethyl oxalate.

In German Offenlegungsschrift 41 23 603, a high selectivity, based both on carbon monoxide and on methyl nitrite, coupled with a high conversion, is achieved by using a palladium chloride catalyst with $\delta$-$Al_2O_3$ as the support. However, to maintain the catalytic activity, gaseous hydrogen chloride must be added to the educt mixture in amounts of up to 1000 ppm (by volume). European Patent 503 618 describes the preparation of dialkyl carbonates in a similar manner using a catalyst which contains a platinum metal, at least one element from the group comprising Fe, Cu, Bi, Co, Ni and Sn, at least one other additive from the group comprising V, Mo and W, and at least one halide. A disadvantage of this process is the fact that only low conversions of methyl nitrite are achieved. Moreover, a sometimes considerable deactivation of the catalysts described is observed after only a few hours. If the process is carried out on the industrial scale, this deactivation incurs appreciable extra expenditure on regenerating or changing the catalyst.

SUMMARY OF THE INVENTION

Surprisingly, in the present invention, these disadvantages could be overcome by using the catalyst according to the invention.

A process has been found for the continuous preparation of dimethyl carbonate by reacting carbon monoxide with methyl nitrite in the presence of an inert gas, in the presence of methanol and in the presence or absence of nitric oxide on a supported palladium catalyst at elevated temperature in a continuous gas phase reaction, which process is characterized in that it is carried out at a volume ratio methyl nitrite:carbon monoxide of 0.1:1 to 10:1, a pressure of 0.5 to 6 bar and a temperature of 50°–200° C., the catalyst having been prepared by the application to a suitable support of one or more palladium compounds of the general formula

$$[Pd(N(R^1, R^2, R^3))_n]X^1{}_2 \qquad (I),$$

in which $R^1$, $R^2$ and $R^3$ independently of one another are hydrogen, $C_1$–$C_4$-alkyl, phenyl or $C_7$–$C_{10}$-aralkyl and $R^3$ can additionally be —$A^1$-N($R^4$, $R^5$), wherein —$A^1$— is linear or branched $C_1$–$C_8$-alkylene, $C_2$–$C_8$-alkylene interrupted by —O— or —$NR^6$—, or phenylene, it being possible for $R^2$ and $R^3$ or $R^4$ and $R^5$, together with the N atom which they substitute, to form the imidazoline, piperidine or morpholine system, and $R^4$, $R^5$ and $R^6$ independently of one another being hydrogen or $C_1$–$C_4$-alkyl, and $R^1$, $R^2$ and $R^3$, $R^2$, $R^3$ and $A^1$ or $A^1$, $R^4$ and $R^5$, in each case together with the N atom which they substitute, can be the pyridine or quinoline system, n indicates the total number of Pd-oriented N atoms in the ligands and is 2, 3 or 4, and $X^1$ is one equivalent of fluoride, chloride, bromide, cyanide, nitrate, sulphate, phosphate or $C_1$–$C_6$-carboxylate, optionally in combination with one or more promoters from the group comprising the elements Fe, Co, Ni, V, Nb, Mo, Ta, Ti, Cu and Cr, the rare earths and/or compounds thereof, and/or optionally with one or more promoters from the group comprising alkali metal and alkaline earth metal halides.

DETAILED DESCRIPTION OF THE INVENTION

It is preferable to use a palladium compound of the formula

$$[Pd(N(R^{11}, R^{12}, R^{13}))_n]X^2{}_2 \qquad (II)$$

in which $R^{11}$, $R^{12}$ and $R^{13}$ independently of one another are hydrogen or $C_1$–$C_4$-alkyl, preferably $C_1$–$C_2$-alkyl and particularly preferably methyl, it being possible for $R^{13}$ additionally to be phenyl, benzyl or —$A^2$-N($R^{14}$, $R^{15}$), wherein —$A^2$— is linear or branched $C_2$–$C_6$-alkylene, preferably dimethylene or trimethylene, and it also being possible for $R^{12}$ and $R^{13}$ and independently thereof $R^{14}$ and $R^{15}$, together with the N atom which they substitute, to form the imidazoline, piperidine or morpholine system, $X^2$ is one equivalent of fluoride, chloride, bromide or sulphate, and n is as defined above. $C_1$–$C_4$-Alkyl is for example methyl, ethyl, propyl, isopropyl, butyl or isobutyl, preferably methyl or ethyl. $C_7$–$C_{10}$-Aralkyl is for example benzyl, phenylethyl ($\alpha$ or $\beta$), phenyl -propyl or phenyl -butyl, preferably benzyl. $C_1$–$C_8$-Alkylene or $C_2$–$C_8$-alkylene interrupted by —O— or —$NR^6$— is for example methylene, dimethylene, trimethylene, tetramethylene, hexamethylene, octamethylene, 1-methyl-dimethylene, 1- or 2-methyl-trimethylene, -tetramethylene or -pentamethylene, 2,3-butylene or an analogous alkylene, preferably one having 2–6 C atoms, —$C_2H_4$-O-$C_2H_4$—, —$C_2H_4$-O-$C_2H_4$-O-$C_2H_4$—, $C_2H_4$-NH-$C_2H_4$—, $C_2H_4$-N($CH_3$)-$C_2H_4$— or analogous groups.

In the manner indicated, it is also possible to form heterocyclic N-containing ring systems whose N atoms bond as a ligand to the Pd.

All the supports known to those skilled in the art are suitable for the process according to the invention, examples being activated charcoal, zeolites, aluminosilicates, metal phosphates, oxides, hydroxides and hydrated oxides of aluminium and silicon, kieselguhrs and silicic acids, molecular sieves, diatomaceous earths, montmorillonites, layer silicates, oxides of titanium, zinc, iron and manganese, or heteropolyacids.

The catalyst according to the invention contains at least one or else optionally several promoters from the group comprising the elements Fe, Co, Ni, V, Nb, Mo, Ta, Ti, Cu and Cr, the rare earths and/or compounds thereof, and/or at least one or more promoters from the group comprising alkali metal and alkaline earth metal halides, in a total amount of 0.1 to 4 wt %, based on the total weight of the catalyst.

The catalysts according to the invention can be prepared for example by dissolving palladium halides with alkali metal or alkaline earth metal halides in a suitable solvent such as water, methanol or acetone, and then reacting the resulting solutions with nitrogen compounds of the general formula $$N(R^1R^2R^3) \quad (III),$$

in which $R^1$, $R^2$ and $R^3$ are as defined, or with salts thereof.

The solutions obtained are then applied to the appropriate catalyst support in a manner known to those skilled in the art, for example by impregnation, absorption or spraying.

The promoters from the group comprising the elements Fe, Co, Ni, V, Nb, Mo, Ta, Ti, Cu and Cr and the rare earths, preferably used in the form of their compounds, and/or the promoters from the group comprising alkali metal and alkaline earth metal halides can be applied to said supports either together with said palladium compounds or else separately therefrom. Preferred promoters from the group of elements are Fe, Co, Ni, Cu, V and/or Mo and particularly preferred promoters are Cu, Fe, V and/or Mo or compounds thereof. Preferred alkali metal (alkaline earth metal) halides are the fluorides or chlorides of Li, Na, K, Cs, Be, Mg and/or Ca, particularly preferably those of Li, Na and/or K.

Another possible way of preparing the catalyst according to the invention consists in impregnating the catalyst with a palladium halide solution optionally containing one or more of said promoters or compounds thereof, and treating the resulting product either with a solution of the appropriate amine (II) or with the gaseous amine (II).

The reaction on which the process according to the invention is based takes place according to the following equation:

$$CO + 2MeONO \rightarrow O=C(OMe)_2 + 2NO$$

While it is possible in principle to react carbon monoxide with methyl nitrite in the absence of other gaseous reaction components or reaction aids, for example when the compositions of the mixture lie outside the explosion limits, an inert gas is used according to the invention to dilute the reactants. Examples of inert gases which are suitable for this purpose are noble gases, nitrogen and carbon dioxide, preferably argon, nitrogen and carbon dioxide and particularly preferably nitrogen and carbon dioxide.

The amount of inert gas is 20 to 85 vol %, based on the total volume of gas to be introduced into the reactor. The inert gas and unconverted reactant residues which may be present can be recycled.

The volume ratio of the reactants methyl nitrite and carbon monoxide is 0.1:1 to 10:1, preferably 0.2:1 to 4:1 and particularly preferably 0.3:1 to 3:1.

The gas mixture to be reacted can also contain small amounts of methanol and small amounts of nitric oxide. Methanol and nitric oxide are each in an amount of for example 0 to 10 vol %, independently of one another, based in both cases on the total volume of the gas mixture to be used. Such additions of methanol or nitric oxide can originate for instance from the preparation of the methyl nitrite and, for example, can be introduced with the latter into the reaction gas mixture.

A small amount of an activator can also be added as a reaction aid to the gas mixture to be reacted. Said activators are halogens or hydrogen halides, such as chlorine, bromine, hydrogen chloride or hydrogen bromide, which are added in an amount of 0 to 2000 ppm, preferably 0 to 1000 ppm and particularly preferably 0 to 750 ppm (by volume in each case). It is preferable to add chlorine or hydrogen chloride.

The process according to the invention is carried out at a temperature of 50°–200° C., preferably 70°–170° C. and particularly preferably 75°–150° C., and at a pressure of 0.5–6 bar, preferably 1–6 bar and particularly preferably 1.5–4.5 bar.

EXAMPLES

Definitions

The space-time yield (STY) in [g/(l×h)] for dimethyl carbonate in the example given is calculated according to equation $$STY = \frac{m_{DMC}}{V_{cat} \times t} \quad [g/(l \times h)],$$

where $m_{DMC}$ is the amount of dimethyl carbonate (DMC) formed, $V_{cat}$ is the volume of catalyst and t is the time.

The selectivity S (%) of DMC formation, based on CO, is calculated according to the equation $$S = \frac{n_{DMC}}{n_{DMC} + 2 \times n_{DMO} + n_{MF} + n_{FDA}} \times 100 \, (\%)$$

where $n_{DMC}$ = amount of dimethyl carbonate
$n_{DMO}$ = amount Of dimethyl oxalate
$n_{MF}$ = amount of methyl formate
$n_{FDA}$ = amount of formaldehyde dimethylacetal.

Preparation of the Catalyst (Catalyst 1)

0.835 g of $PdCl_2$ was dissolved in 4 ml of water with the addition of 0.6 g of sodium chloride. 25 ml of a 25% ammonia solution were added at room temperature, with stirring.

100 ml of Norit ROX 0.8 activated charcoal were impregnated with this solution and then dried in a stream of nitrogen.

Preparation of the Catalyst (Catalyst 2)

0.835 g of $PdCl_2$ was dissolved in 29 ml of water with the addition of 0.6 g of sodium chloride. 0.6 g of ethylenediamine was added at room temperature, with stirring.

100 ml of Norit ROX 0.8 activated charcoal were impregnated with the solution and then dried in a stream of nitrogen.

Preparation of the Catalyst (Catalyst 3)

2.67 g of $PdCl_2$, 5.15 g $CuCl_2.2H_2O$ and 5.59 g $(NH_4)_6Mo_7O_{24}.4H_2O$ was dissolved in 54 ml of water 0.25 ml of a 25% ammonia solution were added at room temperature, with stirring. 200 ml of $\delta$-$Al_2O_3$ (SPH 501 of Rhone-Poulenc) were impregnated with the solution and then dried in a stream of nitrogen at 200° C.

Description of the Process 20 ml of catalyst 1 was introduced into a vertical tubular reactor (glass, length 50 cm, diameter 4 cm) packed with Raschig rings.

The glass tube was heated to 120° C. and a gas mixture of 50 vol % of nitrogen, 30 vol % of methyl nitrite, 15 vol % of carbon monoxide and 5 vol % of methanol was passed through with a GHSV of 5000 h$^{-1}$.

The gas flowing out of the reactor was cooled to 5° C. and the condensed phase obtained was examined by gas chromatography.

The uncondensed products were determined by IR spectroscopy and mass spectroscopy. Dimethyl carbonate was formed after 4 h with a space-time yield of STY=180.5 g/(l×h) and a selectivity of S= 97.2%. After 30 h, the space-time yield was STY= 217.8 g/(l×h) and the selectivity was S=89.5%.

When using catalyst 2, dimethyl carbonate was formed after 4 h with a space-time yield of STY=190.1 g/(l×h) and a selectivity of S= 97.6%. After 30 h, the space-time yield was STY= 212.9 g/l (l×h) and the selectivity was S=88.4%.

When using catalyst 3, the reactor temperature was 90° C. and dimethyl carbonate was formed after 4 h with a space-time yield of STY= 136.8 g/l (l× h) and a selectivity of S=99.9%. After 30 h, the space-time yield was STY= 95.9 g/l (l×h) and the selectivity was S=84.5%.

When again using catalyst 3, the reactor temperature was 90° C. and the feed 9as contained, in addition, 1000 pppm HCl, the dimethyl carbonate was formed after 5 h with a space-time yield of STY=744.7 g/l (l×h) and a selectivity of S=99.9%. After 46 h, the space-time yield was STY= 679.6 g/l (l×h) and the selectivity was S=99.9%.

What is claimed is:

1. A process for the continuous preparation of dimethyl carbonate by reacting carbon monoxide with methyl nitrite in the presence of an inert gas, in the presence of methanol and in the presence or absence of nitric oxide on a supported palladium catalyst at elevated temperature in the gas phase, which is carried out at a volume ratio methyl nitrite:carbon monoxide of 0.1:1 to 10:1, a pressure of 0.5 to 6 bar and a temperature of 50°–200° C., the catalyst having been prepared by the application to a suitable support of one or more palladium compounds of the general formula $$[Pd(N(R^1, R^2, R^3))_n]X^1{}_2 \qquad (I),$$

in which

R$^1$, R$^2$ and R$^3$ independently of one another are hydrogen, $C_1$–$C_4$-alkyl, phonyl or $C_7$–$C_{10}$-aralkyl and R$^3$ can additionally be —A$^1$-N(R$^4$, R$^5$), wherein —A$^1$— is linear or branched $C_1$–$C_8$-alkylene, $C_2$–$C_8$-alkylene interrupted by —O— or —NR$^6$—, or phenylene, it being possible for R$^2$ and R$^3$ or R$^4$ and R$^5$, in each case together with the N atom which they substitute, to form the imidazoline, piperidine or morpholine system, and R$^4$, R$^5$ and R$^6$ independently of one another being hydrogen or $C_1$–$C_4$- alkyl, and R$^1$, R$^2$ and R$^3$, R$^2$, R$^3$ and A$^1$ or A$^1$, R$^4$ and R$^5$, in each case together with the N atom which they substitute, can be the pyridine or quinoline system, provided however that R$^1$, R$^2$ and R$^3$ are not hydrogen at the same time, indicates the total number of Pd-oriented N atoms in the ligands and is 2, 3 or 4, and X$^1$ is one equivalent of fluoride, chloride, bromide, cyanide, nitrate, sulphate, phosphate or $C_1$–$C_6$-carboxylate.

2. The process of claim 1 wherein said catalyst is in combination with one or more promoters selected from the group consisting of the elements Fe, Co, Ni, V, Nb, Mo, Ta, Ti, CU and Cr, the rare earths or compounds thereof, and wherein one or more promoters from the group comprising alkali metal and alkaline earth metal halides are optionally present also.

3. The process of claim 2, wherein one or more promoters from the group comprising the elements Fe, Co, Ni, Cu, V and Mo or compounds thereof, and the fluorides or chlorides of the alkali metals and alkaline earth metals Li, Na, K, Cs, Be, Mg and Ca, are used as constituents of the catalyst.

4. The process of claim 3, wherein promoters from the group comprising the elements Cu, Fe, V and Mo or compounds thereof, and the fluorides or chlorides of the elements Li, Na and K, are used as constituents of the catalyst.

5. The process of claim 1, wherein the support is taken from the group comprising activated charcoals, zeolites, aluminosilicates, metal phosphates, oxides, hydroxides and hydrated oxides of aluminium and silicon, kieselguhrs and silicic acids, molecular sieves, diatomaceous earths, montmorillonites, layer silicates, oxides of titanium, zinc, iron and manganese, and heteropolyacids.

6. The process of claim 5, wherein the support is taken from the group comprising activated charcoals, zeolites, alumino-silicates, metal phosphates, aluminium oxides, manganese oxides and heteropolyacids.

7. The process of claim 6, wherein the support is taken from the group comprising activated charcoal or an aluminum oxide.

8. The process of claim 1, wherein a palladium compound of the formula $$[pd(N(R^{11}, R^{12}, R^{13}))_n]X^2{}_2 \qquad (II)$$

is used in which

R$^{11}$, R$^{12}$ and R$^{13}$ independently of one another are hydrogen or $C_1$–$C_4$-alkyl, it being possible for R$^{13}$ additionally to be phenyl, benzyl or —A$^2$-N(R$^{14}$, R$^{15}$), wherein —A$^2$— is linear or branched $C_2$–$C_6$-alkylene, and it also being possible for R$^{12}$ and R$^{13}$ and independently thereof R$^{14}$ and R$^{15}$, together with the N atom which they substitute, to form the imidazoline, piperidine or morpholine system, X$^2$ is one equivalent of fluoride, chloride, bromide or sulphate, and n is as defined in claim 1.

9. The process of claim 8, wherein R$^{11}$, R$^{12}$ and R$^{13}$ independently of one another are hydrogen or $C_1$–$C_2$-alkyl.

10. The process of claim 9, wherein R$^{11}$, R$^{12}$ and R$^{13}$ independently of one another are hydrogen or methyl.

11. The process of claim 8, wherein —A$^2$— is dimethylene or trimethylene.

12. The process of claim 1, wherein an inert gas from the group comprising noble gases, nitrogen and carbon dioxide is used.

13. The process of claim 12, wherein an inert gas from the group comprising argon, nitrogen and carbon dioxide is used.

14. The process of claim 13, wherein nitrogen or carbon dioxide is used as an inert gas.

15. The process of claim 1, wherein chlorine, bromine, hydrogen chloride or hydrogen bromide is added as a reaction aid serving as an activator, in an amount of 0–2000 ppm by volume.

16. The process of claim 15, wherein 0–1000 ppm by volume of the activator are added.

17. The process of claim 16, wherein 0–750 ppm by volume of the activator are added.

18. The process of claim 1, wherein the reaction is carried out in the temperature range 70° to 170° C. and the pressure range 1 to 6 bar.

19. The process of claim 18, which is carried out at 75° to 150° C. and 1.5 to 4.5 bar.

20. The process of claim 1, wherein the proportions by volume in the reactant gas mixture are 5% to 50% of methyl nitrite, 10% to 30% of carbon monoxide and 20% to of added inert gas.

21. The process of claim 20, wherein the proportions by volume in the reactant gas mixture are 15% to 45% of methyl nitrite, 10% to 25% of carbon monoxide and 45% to 70% of added inert gas.

\* \* \* \* \*

UNITED STATES PATENT AND TRADEMARK OFFICE
CERTIFICATE OF CORRECTION

PATENT NO. : 5,498,744
DATED : March 12, 1996
INVENTOR(S) : Jentsch, et al.

It is certified that error appears in the above-indentified patent and that said Letters Patent is hereby corrected as shown below:

Col. 5, line 64   Delete " phonyl " and substitute -- phenyl --

Col. 8, line 9    After " to " (second occurrence) insert -- 85% --

Signed and Sealed this

Sixteenth Day of July, 1996

Attest:

BRUCE LEHMAN

*Attesting Officer*    Commissioner of Patents and Trademarks